United States Patent [19]

Penick et al.

[11] 4,404,414
[45] Sep. 13, 1983

[54] CONVERSION OF METHANOL TO GASOLINE

[75] Inventors: Joe E. Penick, Chappaqua, N.Y.; Sergei Yurchak, Media, Pa.; John C. Zahner, Princeton, N.J.

[73] Assignee: Mobil Oil Corporation, New York, N.Y.

[21] Appl. No.: 425,845

[22] Filed: Sep. 28, 1982

[51] Int. Cl.³ .............................. C07C 1/20; C07C 1/22
[52] U.S. Cl. .................................. 585/469; 585/408; 585/639; 585/733; 585/315
[58] Field of Search ............... 585/408, 409, 469, 638, 585/639, 640, 733

[56] References Cited

U.S. PATENT DOCUMENTS

| | | | |
|---|---|---|---|
| 3,931,349 | 1/1976 | Kuo | 585/310 |
| 3,969,426 | 7/1976 | Owen et al. | 585/409 |
| 4,035,430 | 7/1977 | Dwyer et al. | 585/322 |
| 4,232,179 | 11/1980 | Barrocas | 585/640 |

*Primary Examiner*—Delbert E. Gantz
*Assistant Examiner*—A. Pal
*Attorney, Agent, or Firm*—Michael G. Gilman; Charles J. Speciale; L. G. Wise

[57] ABSTRACT

A methanol-to-gasoline conversion process in which the conversion is conducted in a number of reactors which are fed directly by the charge, preferably in equal proportions. A diluent gas, preferably recycled light hydrocarbons separated from the product, is passed in sequence through each of the beds to carry away the heat of reaction. In this way, a high effective recycle ratio is maintained in each bed although the actual recycle ratio for the entire system is low.

13 Claims, 1 Drawing Figure

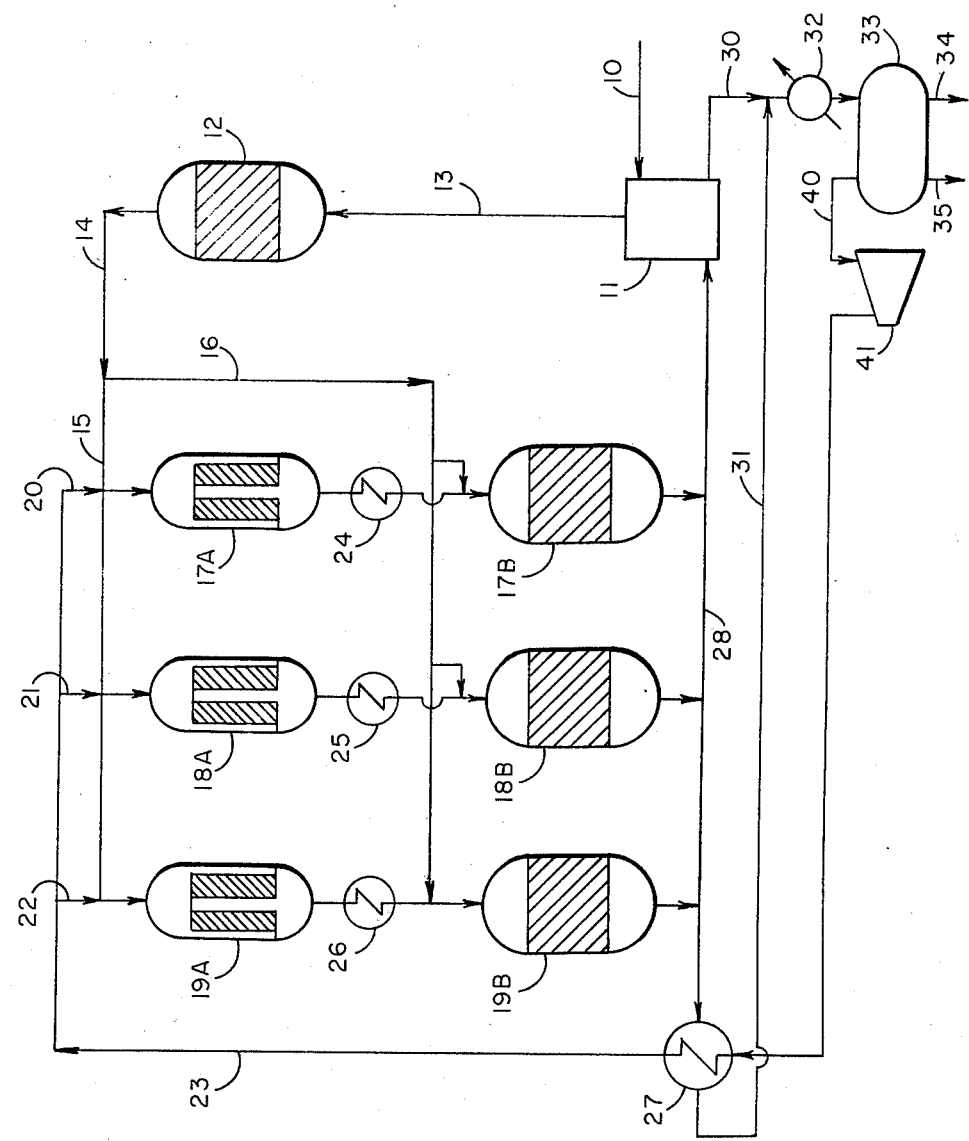

CONVERSION OF METHANOL TO GASOLINE

FIELD OF THE INVENTION

This invention relates to a process for converting methanol and other oxygenated organic compounds to hydrocarbons, especially to gasoline boiling range products.

BACKGROUND OF THE INVENTION

Processes for converting lower alcohols such as methanol to hydrocarbons are known and have become of great interest in recent times because they offer an attractive way of producing liquid hydrocarbon fuels, especially gasoline, from sources which are not of liquid petroliferous origin. In particular, they provide a way by which methanol can be converted to gasoline boiling range products in good yields. The methanol, in turn, may be readily obtained from coal by gasification to synthesis gas and conversion of the synthesis gas to methanol by well-established industrial processes. As an alternative, the methanol may be obtained from natural gas by other conventional processes.

The conversion of methanol to hydrocarbon products may take place in a fluidized bed process as described, for example, in U.S. Pat. Nos. 4,071,573 and 4,138,440, or in a fixed bed as described in U.S. Pat. Nos. 3,998,899, 3,931,349 and 4,035,430. In the fixed bed process, the methanol is usually first subjected to a dehydrating step, using a catalyst such as gamma-alumina, to form an equilibrium mixture of methanol, dimethyl ether (DME) and water. This mixture is then passed over a catalyst such as zeolite ZSM-5 which brings about the conversion to the hydrocarbon products which are mainly in the range of light gas to gasoline. The water may be removed from the methanol dehydration products prior to conversion to hydrocarbons as may the methanol which can be recycled to the dehydration step, as described in U.S. Pat. No. 4,035,430. Removal of the water is desirable because the catalyst may tend to become deactivated by the presence of the water vapor at the reaction temperatures employed, but this step is by no means essential.

In the operation of the fixed bed process, a major problem which has to be dealt with is the thermal balance. The conversion of the oxygenated feed stream (methanol, DME) to the hydrocarbons is a strongly exothermic reaction liberating approximately 1480 kJ. (1400 Btu) of heat per kilogram of methanol. In an adiabatic reactor this would result in a temperature rise which would lead to extremely fast catalyst aging rates or even to damage to the catalyst. Furthermore, the high temperatures which might occur could cause undesirable products to be produced or the product distribution could be unfavorably changed. It is therefore necessary that some method should be provided to maintain the catalyst bed within desired temperature limits by dissipating the heat of the reaction.

A degree of control over the temperature of the catalyst bed can be achieved by suitable choice of bed configuration but this expedient is generally insufficient by itself and other methods must be employed. One particularly efficaceous method is to employ a light gas portion of the hydrocarbon product as recycle, as described in U.S. Pat. No. 3,931,349. The cooled light hydrocarbon gas ($C_4$-) is separated from the products and is compressed and reheated before being mixed with the reactant stream entering the bed of conversion catalyst. Although effective in controlling bed temperature, the expense of cooling the recycle gas, compressing it and re-heating it add to the cost of the conversion, indicating that a reduction in recycle ratio would be economically desirable. The recycle ratio can indeed be decreased but only at the expense of certain disadvantages. Not only will the temperature rise across the catalyst bed be greater, thereby increasing the aging rate of the catalyst but, in addition, the reactor must be operated at a lower and generally less favorable temperature: the outlet temperature must be lowered in order to protect the catalyst from the increased partial pressure of the water which is consequent upon the lower partial pressure of the recycle gas and the inlet temperature must be lowered even further in order to compensate for the greater temperature rise across the catalyst bed. This is generally undesirable because the octane number of the gasoline product is related to reactor temperature with the higher octane products being produced at the higher temperatures. There is also a minimum reactor inlet temperature that must be maintained for the conversion to proceed and consequently, there is a limit on the extent to which the recycle ratio can be reduced. Lower temperatures also bring about an increase in the production of durene although the product can be treated to reduce the proportion of this undesirable product, albeit at extra expense.

An alternative proposal is set out in U.S. Pat. No. 4,035,430. The process described in this patent employs a number of sequential catalyst beds and recycle gas may be injected between the successive beds to control the exotherm. In addition, an interbed injection of methanol or DME may be used as a quench so as to maintain the temperature rise in each bed to about 28° C. (50° F.) with a total rise over the beds to about 110° C. (200° F.). If this is done, however, the conversion in each reactor must be limited to a relatively low value or, alternatively, an extraordinarily high recycle ratio must be used. The first possibility is obviously unattractive and so is the second, for the reasons set out above. It would therefore be desirable to find a way of carrying out the conversion at desirable temperatures with reduced recycle ratios. Such a method is provided by the present invention.

SUMMARY OF THE INVENTION

According to the present invention an oxygenated organic feedstock such as methanol or DME is converted to a hydrocarbon product by charging the oxygenated feedstock to each of a number of fixed bed system reactors or reaction zones in which it is converted to hydrocarbon products by means of contact with a conversion catalyst. Conversion of the oxygenate to hydrocarbon is substantially complete in each reactor and each reactor operates at approximately the same space velocity (WHSV), although this is not necessary. The temperature in the reactors is maintained at the desired value by the use of a diluent which is passed through the reactors in sequence before it is completely cooled and separated from the conversion products.

By operating in this way, the recycle ratio of diluent to oxygenate charge to each reactor is maintained at a sufficiently high value because only a portion of the entire oxygenate is charged to each reactor even though all the recycled diluent passes through the reactor. By this means high reactor temperatures may be used with substantially complete conversion of the oxygenate in each reactor. However, on the basis of the total oxygenate feed, the recycle ratio is reduced by a factor proportionate to the number of reactors in the sequence e.g. is halved with two reactors, thereby enabling a corresponding reduction in operating costs to be made.

The reactor system arrangement may be regarded as being operatively connected in parallel for the oxygenated feed and series for the diluent although, obviously, the primary stage effluent reaction products pass in series through the secondary stage reactors with the diluent. This effects a further effective increase in diluent in the reactors after the first because the greater mass of inert or substantially inert material (diluent plus non-reactive conversion products) passing through the downstream reactors is available to carry away the heat generated in the downstream beds. Thus, for example, if the recycle ratio on the first of a two-bed reactor series is, say 9:1, the ratio of recycle gas in the primary stage effluent together with oxygenate conversion compounds can provide increased diluent effect with respect to an equivalent amount of fresh oxygenated feedstock added to the secondary stage reactors. The overall recycle ratio for the system as a whole, i.e. considering the total amount of reactant charged to both beds, will be about 4.5:1, thereby achieving the desired economy of operation. Because the reaction products will act as a diluent in successive beds after the first, some recycle gas may, if desired, be withdrawn between the successive reactors if a constant recycle ratio in each bed is to be maintained.

DRAWINGS

The single FIGURE of the accompanying drawings is a simplified flowsheet of the present process.

DETAILED DESCRIPTION

Starting Materials

The present process is useful for the conversion of a number of differing oxygenated organic compounds into hydrocarbon products where the conversion is carried out by an exothermic catalytic reaction. The division of the feedstock between a number of reactors with sequential transfer of the diluent from one reactor to the next enables the exotherm to be controlled with a higher effective diluent ratio in each reactor but a low recycle ratio in the system as a whole. The principle is therefore applicable to all reactions of this kind where it is desirable to maintain a given temperature rise in the reactors but, at the same time, to maintain a low recycle ratio in the system as a whole for economic or other reasons. The process is therefore useful for the conversion of aliphatic compounds including lower alcohols such as methanol, ethanol and propanol, ethers such as DME and diethyl ether, ketones such as acetone, methyl ethyl ketone aldehydes such as acetaldehyde, esters such as methyl formate, methyl acetate and ethyl acetate, carboxylic acids such as acetic acid, bulyric acid and their anhydrides e.g. acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions. The product in each case will be a hydrocarbon mixture ranging from light gas to heavier fractions ($C_{10+}$) but will generally be concentrated in the gasoline boiling range ($C_5$-220° C.). The process is particularly useful in the catalytic conversion of methanol to hydrocarbons in the gasoline boiling range and, for convenience, the process will be described below with reference to such a process although it should be remembered that the principles are applicable to a broader range of conversion, as set out above.

If methanol is used as the starting material for the process it is preferred to subject it to an initial dehydration step to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred. It is possible to dehydrate only part of the methanol with, for example, the dehydration product going to one reactor and the raw methanol going to another, as described below.

Process Outline

The FIGURE shows a simplified schematic flowsheet for the conversion of methanol to gasoline. Crude methanol, which may contain up to about 20% by weight water, the amount depending upon the source of the methanol, is fed by inlet 10 to the methanol heater 11 in which it is raised to a suitable temperature for the ensuing dehydration step. From heater 11 the heated methanol goes to dehydration reactor 12 through pipeline 13. In reactor 12, the methanol passes over a dehydration catalyst such as gamma-alumina, to form an essentially equilibrium mixture of methanol, water and dimethyl ether (DME). Because the dehydration reaction is itself exothermic, the temperature of the dehydration products leaving the reactor is higher than the temperature of the methanol feed. The temperature of the mixture leaving the dehydration reactor is adjusted by addition of recycle gas to a temperature suitable for the conversion to hydrocarbons which takes place in the next stage.

From dehydration reactor 12, the products leave by way of pipe 14 and are then split into two approximately equal streams in pipes 15 and 16. The flow from pipes 15 and 16 is then divided between the requisite number of conversion reactors with the flow from pipe 15 going to the radial-flow primary reactors 17A, 18A, 19A and from pipe 16 to the axial-flow secondary reactors 17B, 18B, 19B. The FIGURE shows that three series of reactors are in use, 17A, 17B; 18A, 18B; 19A, 19B, but obviously a greater or lesser number could be used, depending upon the throughput desired and in addition, spare reactors may be provided to allow for servicing and repairs to be made. In each series of reactors shown in the drawing, the reactors are arranged one-on-one with one secondary reactor 17B, 18B and 19B for each first or primary reactor 17A, 18A, 19A. If more than two conversion reactors, i.e. not the dehydration reactor, are used in sequence, all the conversion reactors, except the last one, are radial flow reactors. The last reactor in such a sequence is an axial flow reactor. Radial reactors are preferred for their low pressure drop in order to maintain adequate flow rates through the secondary and any subsequent reactors in the same series. On the other hand, the pressure drop across the final reactor in the series (here, the secondary reactor) need not be maintained at the possible lowest value and because of this, axial flow reactors may be used.

In the primary reactors, the methanol/DME conversion is substantially complete. Charge is converted to hydrocarbons in an exothermic reaction over the conversion catalyst. The exotherm is controlled by means of a diluent which is fed into the primary reactors through pipes 20, 21 and 22, supplied by pipe 23. The reaction products leave the primary reactors together with the diluent and pass through the interreactor heat exchangers 24, 25, 26 which bring the flowstreams to the desired inlet temperature for the secondary reactors. The heat given up in these exchangers may be used in the methanol heater 11, for steam generation or other purposes or may be rejected. Additional cooling may also be provided by directly quenching with liquid methanol introduced at this point through a suitable inlet (not shown). The direct quenching may also be used as an alternative to the cooling provided by heat exchangers 24, 25 and 26.

In the secondary conversion reactors 17B, 18B, 19B, the charge which enters by way of pipe 16 is converted to hydrocarbons in the same way as the charge in the primary reactors. The reaction products leave the secondary reactors and the heat from the product stream is recovered in methanol heater 11 and recycle gas heat exchanger 27, both connected to the secondary reactor outlets by way of pipe 28. After giving up their high quality heat in the methanol heater and the recycle gas heat exchanger, the reaction products pass by way of pipes 30 and 31 to cold water cooler 32 to give up their low quality heat. The cooled products then pass to product separator 33 in which the liquid hydrocarbon products are separated from water and light hydrocarbon gases. The liquid hydrocarbons are drawn off through discharge 34 and the water through discharge 35.

The light hydrocarbon gases primarily $C_4$- which are to be used as diluent are withdrawn from product separator 33 through outlet 40 and then pass to compressor 41 where they are brought to a suitable pressure to match the inlet pressure at the primary conversion reactors. From compressor 41, the diluent gas passes to recycle gas heat exchanger 27 where it is heated by heat exchange with the reaction products from the secondary reactors. The heated recycle gas then passes as diluent from heat exchanger 27 to the primary reactor inlets 20, 21 and 22, as previously described.

Process Conditions

In the first step of the process in its preferred form the methanol is dehydrated to form an equilibrium mixture of methanol, DME and water. For this purpose, the crude methanol is heated to a temperature which is sufficient to sustain the dehydration reaction, suitably to a temperature of at least 285° C. (545° F.) at the inlet to the dehydration reactor, normally to a temperature of 290° C. to 370° C. (550° F. to 700° F.). The actual temperature used may be adjusted according to the water content of the methanol. For example, with a methanol water content of 17 percent, as is typical for methanol produced from natural gas, a temperature of about 315° C. (about 600° F.) will be preferred but if the water content is as low as 4 or 5 percent, temperatures of about 290° C. (about 560° F.) will be preferred for this step of the reaction. At temperatures within this range, the exothermic dehydration reaction which liberates approximately 15 to 20% of the total heat generated in the complete conversion reaction, will become self-sustaining.

The catalyst used for the dehydration will normally be gamma alumina but other heterogenous acidic catalysts may also be used, for example, eta-alumina, silica-alumina or an acidic zeolite such as the zeolites described below. Gamma alumina is, however, preferred. At the recommended reactor temperatures described above, hydration of the preferred alumina catalyst is avoided and excessive aging rates avoided. The catalyst is suitably contained in an axial flow reactor.

The equilibrium mixture of methanol, water and DME produced by the dehydration of the methanol may be separated prior to passing to the conversion reactors. Complete or partial separation into constituent product streams of water, methaol and DME may be carried out as described in U.S. Pat. No. 4,035,430 by condensation or fractionation, depending upon the degree of purity desired. Removal of at least the water is desirable because the conversion catalysts used in the next stage usually become deactivated under the hydrothermal reaction conditions encountered in the conversion. Although it is impossible to eliminate the presence of water vapor completely from the conversion because water is a by-product, the removal of water from the charge will lead to a reduction of the water vapor partial pressure in the conversion reactors and will, accordingly, lead to an increase in the useful life of the catalyst. If the dehydration products are separated in this way, the methanol may be recycled to the dehydration step or it may be used as a direct interstage quench between the primary and secondary conversion reactors as described above.

The dehydration products are then passed to the conversion reactors where the conversion to the hydrocarbon products takes place. As mentioned above, the conversion reaction which takes place is essentially the same in each conversion reactor, with the charge (methanol, DME) to each reactor being substantially completely converted in that particular reactor. Thus, the oxygenated charge to the primary reactor or reactors will be completely converted within the primary reactor (or almost so) and the same is true of the oxygenated charge fed to each of the subsequent reactors in each series of sequential reactors. The feed to each series of reactors is preferably equally divided between each reactor in the series but other divisions may also be made if desired; for example because the mass flow rate through each reactor increases with the sequential additions of charge, a more equal distribution of mass flow may be achieved by charging relatively more to the primary reactor and any other reactor preceding the final one. However, equal division of the charge is preferred even though reactor size (or number of parallel reactors) will have to be adjusted at each stage in order to cope with the increased mass flow. The quantity of catalyst in the primary reactor may be different from that in the secondary reactor; generally, it will be preferable to use more catalyst relative to the oxygenate charge in the secondary reactor than in the primary reactor since the water which is produced as a by-product of the reaction tends to inhibit the conversion.

If desired, the dehydration step may be omitted and the methanol charged directly to the conversion reactors where it will be converted directly to hydrocarbons. However, the use of a separate dehydration reactor is desirable because it enables the exotherm to be more easily controlled and, in addition, offers the possibility of separating the water prior to the conversion reactors, thereby reducing the water partial pressure in the conversion reactors. Reduction of the water partial pressure is desirable because of the resultant increase in effective catalyst life and also because it enables the catalyst to be operated at a higher temperature without encountering accelerated aging. As described below in the Examples, some of the methanol charge may be dehydrated and some charged directly to the conversion reactor or reactors.

Because the oxygenated charge may be fed into the reactors in different forms, e.g. methanol and DME, it will often be convenient, for purposes of calculating recycle ratio and other factors, to base the calculators upon a single equivalent charge. For example, if both methanol and DME are fed to the reactors, the total charge may be reduced to a basis of "methanol equivalents" in which one mole of DME is equal to two methanol equivalents. Thus, the reactant flow at any point may be readily reduced to a single value from which others may be derived, e.g. recycle ratio.

The conversion takes place in the manner described in U.S. Pat. Nos. 3,998,899, 3,931,349 and 4,035,430 to which reference is made for details of the conversion. The conversion is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica:alumina ratio is correctly determined.

Preferred zeolites which have the specified values of Constraint Index and silica:alumina ratio include zeolites ZSM-5, ZSM-11, ZSM-12, ZSM-35, ZSM-38 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), 4,046,859 (ZSM-38) and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g. by heating at over 500° C. for 1 hour or more. The hydrogen form can then be obtained by base exchange with ammonium salts followed by calcination e.g. at 500° C. in air. Other cations e.g. metal cations can be introduced by conventional base exchange techniques.

The conversion of the oxygenated charge over the catalyst is a strongly exothermic reaction which, if unchecked, would result in a substantial temperature rise in the catalyst, resulting in the production of undesired products, damage to the catalyst, or both. In order to contain the exotherm, a diluent is used. This diluent is preferably the light hydrocarbon gas produced in the conversion, recycled in the appropriate amount. The recycle gas, preferably the $C_4$- portion of the hydrocarbon products, may suitable be obtained by separation in a high pressure separator. The diluent passes through each catalyst bed in a given series of beds in turn, with additional fresh oxygenate charge being added to each bed. Conversion of the charge in each bed is substantially complete so that the reactant mass which is converted in each bed is essentially equivalent to the amount of oxygenate charged to that bed. The diluent gas passes essentially unchanged from bed to bed to dissipate and carry away the heat of reaction and in doing this is assisted by non-reactive conversion products from any preceding beds. Because only a portion of the total charge is converted in any given bed, the effective recycle (diluent) ratio for any single bed is relatively high but because the recycle gas is used for several beds in succession, the recycle ratio for the process and system as a whole, is much lower, thereby achieving the desired economies of operation. The overall recycle ratio is suitably from 4:1 to 16:1, preferably about 4:1 to 6:1 calculated on the molar basis of recycle gas and total organic chargestock, calculated on a basis of organic charge, e.g. methanol equivalents. Normally, the single reactor molar recycle ratio, calculated in this way, i.e. recycle gas to total oxygenate charged on a molar basis, will not exceed 15:1 and preferably will be in the range of 8:1 to 12:1. With methanol/DME feeds, ratios between 5.5:1 and 15:1, preferably 8:1 to 12:1, (e.g. 10:1 or 11:1, on a methanol equivalent basis) and particularly useful. Because the oxygenate charge is divided among the individual beds in the series, the effective recycle ratio in each individual bed will be higher than the overall ratio because only a portion of the total charge is converted in each bed, e.g. in a two-bed series operating at an overall recycle ratio of 6:1, the effective recycle ratio in each bed will be 12:1 because the amount of reactant charged to each bed is one-half the total reactant but the entire amount of recycle gas passes through each bed in turn. This is an approximation because it considers only the diluent gas actually passing in the recycle circuit whereas the non-reactive conversion products from the first bed will also act as a diluent in the second bed and the products from the second bed in the third and any subsequent beds and so on. This will produce successively greater effective recycle ratios in each bed after the first; thus, in the two-bed series mentioned above with an overall ratio of 6:1, the effective ratio in the first bed will be 12:1 and in the second will be rather more than 12:1 when allowance is made for the diluent effect of the reaction products.

Because the amount of oxygenate charged to each reactor is generally the same, the space velocity (WHSV) in each reactor will generally be the same but obviously, if different amounts are charged to each reactor or if the reactors contain different amounts of catalyst, the space velocity will differ correspondingly. In any event, the space velocity should normally be kept within the range of 0.1 to 20, preferably 0.5 to 10 WHSV (weight of total oxygenate charge equivalent basis to weight of catalyst per hour), to maintain the desired temperature rise in the beds. Generally, a minimum temperature rise of at least 45° C. (80° F.), preferably at least 60° C. (about 110° F.) should be sought. The maximum temperature rise will depend upon the selectivity of the catalyst for the desired products and the relationship between selectivity and temperature; it will also be dependent upon other factors such as the hydrothermal stability of the catalyst and engineering factors. In general, the temperature rise in the first bed will be held to a maximum of 140° C. (about 250° F.), preferably to less than 110° C. (200° F.). In subsequent beds the temperature rise will be rather less because of the greater mass flow rate in subsequent beds. For example, a temperature rise of about 50° C. (90° F.) in the first bed of a two-bed reactor series will lead to a rise of about 45° C. (about 80° F.) in the second bed.

Inlet temperatures of 300° C. to 400° C. (about 570° F. to 750° F.) for the first reactor are normally suitable and are preferably from 330° C. to 370° C. (about 625° F. to 700° F.) although in certain processes temperatures as low as 275° C. (about 530° F.) may be desirable. Control of the inlet temperature to subsequent reactors may be achieved by the use of interstage heat exchangers or by the injection of a diluent at a lower temperature, such as liquid methanol, as described above. Although the temperature rise in the secondary and any subsequent reactors will be less than that in the first reactor, similar or somewhat lower reactor inlet temperatures should be used for these reactors because of the higher water partial pressure which will tend to prevail but this will depend also upon the engineering factors of the system.

The inlet temperature to the first or primary reactor will be governed by the temperature of the oxygenate charge and that of the diluent gas. The temperature of the oxygenate charge will depend upon the conditions employed in the dehydration reactor. The temperature of the diluent gas may be varied within rather wide limits by various means but since the diluent is usually recycle light hydrocarbon gases obtained at low temperature from the product separator, its temperature may readily be controlled by heat exchange with the reaction products from the final reactor, as described above. Normally, the recycle gas will be at a lower temperature than the oxygenate charge. Typical temperatures will be from 370° to 455° C. (about 700° to 850° F.), preferably 390° to 420° C. (about 735° to 790° F.) for the dehydration reactor effluent and 295°–400° C. (about 565° to 750° F.), preferably 310° to 370° C. (about 590° to 700° F.) for the recycle gas.

As mentioned above, space velocities of 0.1 to 20 preferably 0.5 to 10 WHSV, are generally suitable. The pressure as such is not a critical feature of the process and will normally be chosen according to the nature of the process itself and the engineering factors in question such as the design pressure drop the catalyst beds and other equipment. Because the nature of the products may vary with pressure-related factors such as the oxygenate/water partial pressure ratio, it may be desirable to adjust the pressure so as to obtain the desired products in the desired ratio; for example, since the amount of durene produced is proportional to the partial pressure of methanol, if may be desirable to decrease the methanol partial pressure in order to minimize durene production. However, in most cases the reactor inlet pressure will be from 500 to 15,000 kPa (about 60 to 2160 psig), more commonly from 500 to 3000 kPa (about 60 to 420 psig).

Because catalyst aging is dependent upon the water partial pressure in the reactor, the catalyst will tend to age more rapidly in the secondary and any subsequent reactors as water is formed as a by-product of the conversion reaction which occurs. For this reason, temperatures in the secondary reactor are somewhat lower than in the primary reactor or, alternatively, interstage separation of water may be desirable e.g. by cooling and fractionation.

Separation of the products from the water and fractionation of the hydrocarbons into products may be made in the conventional manner, as described, for example, in U.S. Pat. Nos. 3,998,898, 3,998,899, 3,931,349 and 4,035,430 to which reference is made for further details of the process.

The invention is illustrated in the following Examples in which all parts, proportions and percentages are by weight unless the contrary is stated.

EXAMPLES 1 AND 2

An apparatus similar to that shown in the FIGURE and comprising a methanol charging system, a dehydration reactor, two conversion reactors connected in series, a high pressure separator, a gas recycle system and a product collection system was set up. The apparatus was constructed so that approximately half the methanol charge was fed to the dehydration reactor which contained gamma-alumina as the dehydration catalyst. The product from the dehydration reactor was mixed with light hydrocarbon recycle gas and passed into the first conversion reactor which contained ZSM-5 conversion catalyst in the form of an extrudate with alumina binder. The other half of the methanol charge was fed directly to the second conversion reactor where it mixed with the effluent from the first conversion reactor before contacting the ZSM-5 extrudate conversion catalyst in the second reactor. The effluent from the second conversion reactor was cooled and passed into the high pressure separator. The liquid hydrocarbon and aqueous products were separated and sent to product receivers. Most of the hydrocarbon gas leaving the separator was recycled to the first conversion reactor so that it passed through the two conversion reactors in sequence. Some gas was removed from the recycle system as gas product after the high pressure separator.

The operating conditions employed are shown in Table 1 below and the product yields in Table 2. The operating conditions differed primarily in the recycle ratio, the temperatures of the conversion reactors and the separator temperature. The hydrocarbon product, in both cases comprises primarily gasoline of high octane number.

These Examples show that it is possible to operate the conversion without initial dehydration of the methanol charge; although only the feed to the second conversion reactor was made without dehydration, the entire process could be operated without dehydration with the methanol charge being fed directly to the conversion reactors.

TABLE 1

| Operating Conditions | Ex. 1 | Ex. 2 |
|---|---|---|
| Catalyst Fill | | |
| Dehydration Reactor, g. | 10.0 | 35.7 |
| Conversion Reactor, No. 1, g. | 31.4 | 30.9 |
| Conversion Reactor, No. 2, g. | 31.2 | 30.3 |
| Methanol/Water Charge, Wt/Wt | 84/16 | 83/17 |
| Pressure, kPa | 2170 | 2170 |
| Overall Recycle Ratio (mol recycle gas/mol total methanol equivs) | 4.7 | 6.1 |
| Separator Temp., °C. | 52 | 18 |
| Separator Pressure, kPa | 2170 | 2170 |
| Dehydration Reactor (For Conv. Reactor 1) | | |
| Inlet temp., °C. | 315 | 305 |
| Outlet temp., °C. | 400 | 390 |
| WHSV, hr$^{-1}$ | 6.0 | 1.7 |
| Conversion Reactor No. 1 | | |
| Inlet temp., °C. | 340 | 360 |
| Outlet temp., °C. | 405 | 415 |
| WHSV, hr$^{-1}$ | 1.9 | 1.9 |
| Effective recycle ratio (mol recycle gas/mol methanol equivs to conv. reactor No. 1) | 9.4 | 12.3 |
| Conversion Reactor No. 2 | | |
| Inlet temp., °C. | 330 | 350 |
| Outlet temp., °C. | 395 | 405 |
| WHSV, hr$^{-1}$ | 1.9 | 1.9 |
| Effective Diluent Ratio (mols diluent/mol methanol equivs to conv. reactor No. 2) | 10.8 | 13.8 |

TABLE 2

| Product Yields | Ex. 1 | Ex. 2 |
|---|---|---|
| Yields on Methanol, Wt. % | | |
| Hydrocarbons | 43.2 | 42.9 |
| Water | 56.5 | 56.8 |
| CO + CO$_2$ + H$_2$ | 0.3 | 0.3 |
| Methanol | 0.0 | 0.0 |
| Dimethyl Ether | 0.0 | 0.0 |
| | 100.0 | 100.0 |
| Hydrocarbon Product, Wt. % | | |
| C$_1$ + C$_2$ | 1.9 | 1.7 |
| C$_3$° | 5.9 | 5.9 |
| C$_3$= | 0.2 | 0.4 |
| iC$_4$° | 8.7 | 10.1 |
| nC$_4$° | 3.0 | 3.0 |
| C$_4$= | 0.7 | 1.5 |
| C$_5$+ Gasoline | 79.5 | 77.4 |
| | 100.0 | 100.0 |
| 9 RVP Gasoline (Incl. C$_3$ and C$_4$ alkylate) | | |
| Octane, R + O | 92 | 93 |
| Yield, Wt. % of Hydrocarbons | 84.5 | 83.6 |

We claim:

1. A process for the conversion of an oxygenated organic compound to a gasoline boiling range hydrocarbon product, which comprises:

(i) charging a portion of the oxygenated organic compound to each of a plurality of reaction zones containing a ZSM-5 type conversion catalyst in primary and secondary stages of a multi-stage reactor system, (ii) contacting the portion of oxygenated organic compound with the conversion catalyst in each of the primary and secondary stages to form a hydrocarbon product in each reaction zone, (iii) separating a recycle stream of light diluent gas from the hydrocarbon product, and (iv) passing the recycle stream of diluent gas through each of the stages in sequence at an overall molar ratio of the diluent gas to the total amount of oxygenated organic compound fed to the reaction zones through which the diluent gas passes of about 4:1 to 6:1.

2. A process according to claim 1 in which the oxygenated organic compound charged to each reaction zone is substantially completely converted to hydrocarbon product within the reaction zone to which it is charged.

3. A process according to claim 1 in which the oxygenated organic compound comprises methanol which is fed to the plurality of reaction zones as such or in the form of dimethyl ether.

4. A process according to claim 1 in which the temperature rise in the first of the sequence of reaction zones through which the diluent gas passes is at least 45° C.

5. A process according to claim 1 in which the temperature rise in the first of the sequence of reaction zones through which the diluent gas passes is at least 60° C.

6. A process according to claim 1 in which the methanol is dehydrated over a gamma alumina catalyst in a dehydration reactor and subsequently charged to at least one reaction zone for further conversion to hydrocarbon product.

7. A process according to claim 1 in which the dehydration products are converted to hydrocarbons over a crystalline aluminosilicate zeolite catalyst having a silica:alumina ratio of at least 12:1 and a Constraint Index of 1 to 12.

8. A process according to claim 7 in which the zeolite is ZSM-5.

9. In a process for converting methanol to a gasoline boiling range hydrocarbon product by dehydrating the methanol to form a dehydration product comprising dimethyl ether, contacting the dehydration product with a zeolite conversion catalyst under conversion conditions of elevated temperature to form the hydrocarbon product, forming a recycle stream of hydrocarbon diluent gas from the product and passing the recycle stream over the conversion catalyst with the methanol dehydration product, the improvement comprising:

(i) charging a portion of the methanol dehydration product to each of a plurality of fixed beds of the zeolite conversion catalyst in primary and secondary reaction zones of a multi-stage reactor system, (ii) converting the portion of dehydration product to hydrocarbon product in each of said reaction zones, (iii) withdrawing as effluent from the primary zone product from each bed together with recycle diluent gas (iv) passing the primary zone effluent through at least one successive secondary zone in a sequence, (v) circulating the recycle diluent gas in sequence through each reaction zone and withdrawing the recycle diluent from the final zone of the sequence, (vi) withdrawing the hydrocarbon product from the final zone of the sequence.

10. A process according to claim 9 in which there are two beds in the sequence.

11. A process according to claim 9 in which the dehydration product is charged in substantially equal proportions by weight to each of the zones.

12. A process according to claim 9 in which effluent from each zone prior to the final zone of the sequence is partially cooled prior to entering the next bed.

13. In a process for converting methanol feedstock to a gasoline boiling range hydrocarbon product by contacting feedstock consisting essentially of methanol or dimethyl ether dehydration product with a zeolite conversion catalyst under conversion conditions of elevated temperature to form the hydrocarbon product, forming a recycle stream of hydrocarbon diluent gas from the product and passing the recycle stream over the conversion catalyst with the feedstock, the improvement comprising:

(i) charging the feedstock to each of a plurality of reaction zones arranged in parallel, (ii) converting the feedstock in each bed to the hydrocarbon product by contact with the zeolite conversion catalyst, (iii) circulating the recycle stream of hydrocarbon diluent gas through each of the reaction zones in series to carry away heat of reaction produced by the conversion at an overall molar recycle ratio of about 4:1 to 6:1 based on total methanol equivalents in the feedstock, (iv) withdrawing the hydrocarbon product from each bed together with the recycle diluent gas.

* * * * *

UNITED STATES PATENT AND TRADEMARK OFFICE
CERTIFICATE OF CORRECTION

PATENT NO. : 4,404,414

DATED : September 13, 1983

INVENTOR(S) : J.E. Penick, S.Yurchak and J.C. Zahner

It is certified that error appears in the above—identified patent and that said Letters Patent is hereby corrected as shown below:

Column 2, line 36, after "over" insert --all--.

Column 2, line 52, before "reaction" insert --system--.

Column 2, line 52, before "reactors" delete "system".

Column 6, line 12, delete "methaol" and insert --methanol--.

Column 7, line 10, delete "calculators" and insert --calculations--.

Column 8, line 31, delete "suitable" and insert --suitably--.

Column 8, line 58, delete "and" and insert --are--.

Column 10, line 16, delete "if" and insert --it--.

Signed and Sealed this

Second Day of April 1985

[SEAL]

Attest:

DONALD J. QUIGG

Attesting Officer     Acting Commissioner of Patents and Trademarks